United States Patent
Ryu et al.

(10) Patent No.: US 9,169,180 B1
(45) Date of Patent: Oct. 27, 2015

(54) METHOD FOR PREPARING AN ANHYDROSUGAR ALCOHOL USING HYDROL

(71) Applicant: SAMYANG GENEX CORPORATION, Seoul (KR)

(72) Inventors: Hoon Ryu, Daejeon (KR); Young Jae Jung, Daejeon (KR); Jin Kyung Kim, Daejeon (KR); Do Hyun Kyung, Daejeon (KR); Hyuk Min Park, Incheon (KR); Seong Ho Cho, Seoul (KR)

(73) Assignee: SAMYANG GENEX CORPORATION, Seoul (KR)

( * ) Notice: Subject to any disclaimer, the term of this patent is extended or adjusted under 35 U.S.C. 154(b) by 0 days.

(21) Appl. No.: 14/651,726

(22) PCT Filed: Dec. 12, 2013

(86) PCT No.: PCT/KR2013/011555
§ 371 (c)(1),
(2) Date: Jun. 12, 2015

(87) PCT Pub. No.: WO2014/092490
PCT Pub. Date: Jun. 19, 2014

(30) Foreign Application Priority Data

Dec. 14, 2012 (KR) ........................ 10-2012-0146669

(51) Int. Cl.
*C07C 29/132* (2006.01)
*C07C 31/18* (2006.01)
*C07C 29/34* (2006.01)

(52) U.S. Cl.
CPC ............... *C07C 29/132* (2013.01); *C07C 31/18* (2013.01); *C07C 29/34* (2013.01)

(58) Field of Classification Search
CPC ........ C07C 31/18; C07C 29/94; C07C 29/132
USPC .......................................... 568/701, 868, 916
See application file for complete search history.

(56) References Cited

U.S. PATENT DOCUMENTS

2003/0097028 A1   5/2003   Fuertes

FOREIGN PATENT DOCUMENTS

| KR | 2003-0010905 A | 2/2003 |
| KR | 10-2004-0070173 A | 8/2004 |
| KR | 10-2011-0076268 A | 7/2011 |
| KR | 10-1079518 B1 | 11/2011 |
| KR | 10-2012-0066904 A | 6/2012 |
| WO | WO 2012/081785 A1 | 6/2012 |

OTHER PUBLICATIONS

International Search Report, issued in PCT/KR2013/011555, mailed Mar. 26, 2014.
Xia et al., "Sulfated copper oxide: An efficient catalyst for dehydration of sorbitol to isosorbide", Catalysis Communications, 2011, vol. 12, pp. 544-547.

*Primary Examiner* — Elvis O Price
(74) *Attorney, Agent, or Firm* — Birch, Stewart, Kolasch & Birch, LLP

(57) ABSTRACT

The present invention relates to a method for preparing an anhydrosugar alcohol using hydrol (namely, a crystalline mother liquor remaining after obtaining crystalline glucose from a crude glucose liquor). More particularly, the present invention relates to a method for preparing an anhydrosugar alcohol in a method for performing a dehydration reaction on the hydrogenated sugar so as to convert the hydrogenated sugar to an anhydrosugar alcohol, wherein the method for preparing an anhydrosugar alcohol is configured to use, as at least a portion of the hydrogenated sugar, the product obtained from the hydrogenation of the hydrol which is a by-product or waste generated during the production of glucose, thus relatively lowering the cost for a material as compared with a case of using a high purity raw material (for example, high purity sorbitol), to thus improve economical advantages, and further reduce the amount of waste and cost for disposal of the waste during the production of glucose.

13 Claims, No Drawings

METHOD FOR PREPARING AN ANHYDROSUGAR ALCOHOL USING HYDROL

TECHNICAL FIELD

The present invention relates to a method for producing anhydrosugar alcohol by using hydrol (i.e., the mother liquor remaining after obtaining glucose crystals from crude glucose liquid), and more specifically a method for producing anhydrosugar alcohol through converting hydrogenated sugar to anhydrosugar alcohol by dehydration reaction, wherein a product of hydrogenation reaction of hydrol—which is a byproduct or waste generated in glucose production—is used as at least a part of the hydrogenated sugar, thereby the cost for raw material can be relatively lowered as compared with the use of highly pure material (e.g., highly pure sorbitol) and thus the economic feasibility can be improved and the amount of waste generated in glucose production and the cost for disposal thereof can be reduced.

BACKGROUND ART

Hydrogenated sugar (also referred to as "sugar alcohol") means a compound obtained by adding hydrogen to the reductive end group in sugar, and generally has a chemical formula of $HOCH_2(CHOH)_nCH_2OH$ wherein n is an integer of 2 to 5. According to the carbon number, hydrogenated sugar is classified into tetritol, pentitol, hexitol and heptitol (4, 5, 6 and 7 carbons, respectively). Among them, hexitol having 6 carbons includes sorbitol, mannitol, iditol, galactitol, etc. and in particular, sorbitol and mannitol are very useful materials.

Anhydrosugar alcohol has a diol form with two hydroxyl groups in the molecule, and can be produced by using hexitol derived from starch (for example, Korean Patent No. 10-1079518 and Korean Laid-open Patent Publication No. 10-2012-0066904). Because anhydrosugar alcohol is an environmentally friendly material derived from recyclable natural resources, it has received much interest for a long time and researches on its production continue to proceed. Among such anhydrosugar alcohols, isosorbide produced from sorbitol has the widest industrial applicability at present.

Anhydrosugar alcohol can be used in various fields including treatment of heart and blood vessel diseases, medicaments such as patch adhesive, mouthwash, etc., solvents for compositions in the cosmetics industry, emulsifiers in the food industry, etc. In addition, it can increase the glass transition temperature of polymer materials like polyester, PET, polycarbonate, polyurethane, epoxy resin, etc., and improve the strength of such materials. Furthermore, because anhydrosugar alcohol is an environmentally friendly material derived from natural resources, it is very useful in the plastics industry such as bioplastics and the like. It is also known that anhydrosugar alcohol can be used as an adhesive, environmentally friendly plasticizer, biodegradable polymer, and environmentally friendly solvent for water-soluble lacquer.

As such, anhydrosugar alcohol is receiving much interest because of its wide applicability, and the level of practical industrial application thereof is increasing. However, the conventional methods of producing anhydrosugar alcohol have limitations of high cost for the catalyst and raw material used in the dehydration reaction, low conversion rate, and low yields of distillation and purification, etc. Therefore, it is required to develop a technology which can produce anhydrosugar alcohol by a method with improved economic feasibility.

CONTENTS OF THE INVENTION

Problems to be Solved

To resolve the problems of the prior arts as explained above, the present invention has an object of providing a method for producing anhydrosugar alcohol utilizing hydrol—which is a byproduct or waste generated in glucose production—as a raw material, thereby the economic feasibility can be improved and the amount of waste generated in glucose production and the cost for disposal thereof can be reduced.

Technical Means

To achieve the above-stated object, the present invention provides a method for producing anhydrosugar alcohol comprising the step of converting hydrogenated sugar to anhydrosugar alcohol by dehydration reaction, wherein a product of hydrogenation reaction of hydrol is used as at least a part of the hydrogenated sugar.

Effect of the Invention

According to the present invention, it is possible to bring about a relatively lower cost for raw material as compared with the use of highly pure material (e.g., highly pure sorbitol having purity of 90% or higher) while obtaining an equivalent or higher level of conversion rate to anhydrosugar alcohol, thereby the economic feasibility can be improved and the amount of waste generated in glucose production and the cost for disposal thereof can be reduced.

Concrete Explanation to Carry Out the Invention

The present invention is explained in more detail below.

The method for producing anhydrosugar alcohol of the present invention is characterized in that in converting hydrogenated sugar to anhydrosugar alcohol by dehydration reaction, a product of hydrogenation reaction of hydrol is used as at least a part of the hydrogenated sugar.

Hydrogenated sugar, also generally referred to as sugar alcohol, means a compound obtained by adding hydrogen to the reductive end group in sugar. According to the carbon number, hydrogenated sugar is classified into tetritol, pentitol, hexitol and heptitol (4, 5, 6 and 7 carbons, respectively). Among them, hexitol, having 6 carbons, includes sorbitol, mannitol, iditol, galactitol, etc.—in particular, sorbitol and mannitol are very useful materials.

As used herein, the expression "anhydrosugar alcohol" means any material that is obtained by removing one or more water molecules from the original inner structure of said hydrogenated sugar in one or more steps by any method.

As used herein, "hydrol" means the mother liquor remaining after glucose production by crystallizing crude glucose liquid to form glucose crystals (anhydrous or hydrate crystals) and filtering the resulting product to obtain glucose crystals, and it usually contains about 82 to 90% by weight of glucose and about 10 to 18% by weight of oligosaccharides (disaccharides, trisaccharides, tetrasaccharides, etc.).

In the present invention, there is no special limitation in the hydrogenation reaction of hydrol, and any conventional reaction for adding hydrogen to the reductive end group in sugar may be utilized as it is or with proper modification. For example, the hydrogenation reaction of hydrol may be conducted in a manner of adding nickel as a catalyst to hydrol in the presence of nitrogen and elevating the reaction temperature to a temperature between 115° C. and 130° C., adding hydrogen thereto and controlling the pressure to 60 atmospheres, and carrying out the reaction for 30 minutes to 2 hours.

According to an embodiment of the present invention, the resulting product of hydrogenation reaction of hydrol has a sorbitol content of preferably 80% by weight or more (for example, 80 to 88% by weight), and more preferably 84% by weight or more (for example, 84 to 88% by weight). If the sorbitol content in the product of hydrogenation reaction of hydrol is less than 80% by weight, the effect of improving economic feasibility of the anhydrosugar alcohol production process may be insufficient.

In the present invention, at least a part of the hydrogenated sugar to be converted to anhydrosugar alcohol is derived from the product of hydrogenation reaction of hydrol. For example, 10% by weight or more, preferably 30% by weight or more, more preferably 50% by weight or more, even more preferably 80% by weight or more, and most preferably 100% by weight of the hydrogenated sugar to be converted to anhydrosugar alcohol can be derived from the product of hydrogenation reaction of hydrol. Among the total hydrogenated sugar, the remainder excluding the product of hydrogenation reaction of hydrol may be conventional hydrogenated sugar with high purity (for example, highly pure sorbitol with a purity of 90% or higher).

In the present invention, the hydrogenated sugar comprising the product of hydrogenation reaction of hydrol at least in part, is converted to anhydrosugar alcohol by dehydration reaction. There is no special limitation in the method of dehydrating hydrogenated sugar, and any conventionally known method in this field may be utilized as it is or with proper modification.

It is preferable to use an acid catalyst in dehydrating hydrogenated sugar to convert it to anhydrosugar alcohol. As for the acid catalyst, a single acid catalyst such as sulfuric acid, hydrochloric acid, phosphoric acid, etc. can be used, and more preferably, sulfuric acid can be used. Alternatively, an acid mixture of a first acid and a second acid can be used, and more preferably, sulfuric acid can be used as the first acid, and one or more acids selected from the group consisting of methanesulfonic acid, p-toluenesulfonic acid, boric acid, ethanesulfonic acid, benzenesulfonic acid, naphthalenesulfonic acid and aluminum sulfate can be used as the second acid. The acid catalyst is preferably used in an amount of from 0.5 to 10 parts by weight per 100 parts by weight of the hydrogenated sugar. If the amount of acid catalyst is much less than the above range, the conversion time to anhydrosugar alcohol may become excessively long. On the other hand, if the amount of acid catalyst is much greater than the above range, sugar polymer may be increasingly generated and the conversion rate may be lowered.

According to an embodiment of the present invention, the step of converting hydrogenated sugar to anhydrosugar alcohol may be conducted in the presence of an acid catalyst as explained above, at a temperature of from 105 to 200° C. (more preferably, 110 to 150° C.) under a pressure of from 1 to 100 mmHg (more preferably, 1 to 50 mmHg) for 1 to 10 hours (more preferably, 2 to 5 hours), but it is not limited thereto.

In the case of using an acid catalyst during the dehydration reaction of hydrogenated sugar, it is preferable to neutralize the reaction product liquid. The neutralization may be conducted after the dehydration reaction by cooling the reaction product liquid (e.g., to 100° C. or lower) and adding thereto conventional alkali such as sodium hydroxide. The neutralized reaction product liquid preferably has a pH of 6 to 8.

In the present invention, as the anhydrosugar alcohol which is the product of the dehydration reaction, dianhydrohexitol—which is the dehydrated product of hexitol—is preferably obtained, and more preferably the obtained anhydrosugar alcohol is selected from isosorbide (1,4-3,6-dianhydrosorbitol), isomannide (1,4-3,6-dianhydromannitol), isoidide (1,4-3,6-dianhydroiditol) and mixtures thereof. Among them, isosorbide is particularly useful for industrial and medicinal application.

The neutralized product of the dehydration reaction of hydrogenated sugar as obtained above can go through distillation after being pre-treated, if necessary, and subsequent purification procedure to produce an anhydrosugar alcohol product with high purity.

There is no special limitation in the distillation of the product of the dehydration reaction of hydrogenated sugar, and any conventionally known method and device in this field may be utilized as it is or with proper modification. For example, a general condenser-type evaporator or column distillator may be used, or a thin-film evaporator may be utilized for the distillation.

The subsequent purification procedure for the resulting liquid of distillation may be one or more selected from crystallization, decolorization and treatment with ion exchange resin, but it is not limited thereto. There is no special limitation in the order thereof. For these subsequent purification procedures, with no special limitation, any conventionally known method and device in this field for the corresponding treatment procedure may be utilized as it is or with proper modification.

According to an embodiment of the present invention, the distillation may be conducted with using a thin-film evaporator, and the crystallization may be conducted by a crystallization method using acetone solvent or by a melt crystallization method using no solvent. The decolorization may be conducted with using active carbon, and the treatment with ion exchange resin may be conducted with using strong cationic ion exchange resin, strong anionic ion exchange resin, or all of them in this order.

The present invention is explained in more detail through the following Examples and Comparative Examples. However, the Examples are intended to facilitate understanding of the present invention only, and the scope of the present invention is not limited thereby.

EXAMPLES

Example 1

Hydrol generated in glucose production (glucose content: 87% by weight) was subject to hydrogenation reaction using nickel catalyst under the condition of 125° C. temperature and 60 atm pressure to obtain a liquid product with a concentration of 56% by weight (sorbitol content: 85%).

3,000 g of the obtained liquid product of hydrogenation reaction of hydrol was fed into a batch reactor equipped with an agitator and concentrated by heating to 100° C. or higher. 17 g of sulfuric acid (Duksan Chemical) and 7 g of methanesulfonic acid (Duksan Chemical) were added thereto. The reactor was then heated to about 130° C., and dehydration reaction was conducted under a reduced pressure condition of about 45 mmHg for conversion to anhydrosugar alcohol. After the dehydration reaction was completed, the reaction mixture was cooled to 110° C. or lower, and about 45 g of 50% sodium hydroxide solution (Samjeon Pure Chemical) was added thereto to neutralize the resulting reaction liquid. The neutralized resulting liquid was set to be at 100° C. or lower and then concentrated under a reduced pressure condition of 45 mmHg or less for 1 hour or longer to remove the moisture and low-boiling-point substance present in the resulting liquid. The conversion rate to anhydrosugar alcohol was 77.5% according to the gas chromatography analysis result.

Example 2

Other than the fact that 17 g of sulfuric acid and 6 g of p-toluenesulfonic acid instead of methanesulfonic acid were used, the process was conducted in the same manner as in Example 1. The conversion rate to anhydrosugar alcohol was 76.4% according to the analysis result.

Example 3

Other than the fact that 17 g of sulfuric acid and 6 g of boric acid instead of methanesulfonic acid were used, the process was conducted in the same manner as in Example 1. The conversion rate to anhydrosugar alcohol was 76.2% according to the analysis result.

Comparative Example

Other than the fact that 1,700 g of sorbitol with 99 wt % concentration and 95% purity (Samyang Genex Inc.) was used, the process was conducted in the same manner as in Example 1. The conversion rate to anhydrosugar alcohol was 77.2% according to the analysis result.

As can be seen from the results of the above Examples and Comparative Example, in the case of the Examples using a product of hydrogenation reaction of hydrol instead of highly pure sorbitol, the conversion rate was equivalent to or better than that of the Comparative Example using highly pure sorbitol. If the relative cost for raw material is calculated for the relative economic feasibility, Examples 1 to 3 correspond to 80, 81 and 81, respectively, when the Comparative Example is set to 100. Accordingly, it can be known that as compared with the Comparative Example, the Examples of the present invention are more economical processes as a whole.

The invention claimed is:

1. A method for producing anhydrosugar alcohol comprising the step of converting hydrogenated sugar to anhydrosugar alcohol by dehydration reaction, wherein a product of hydrogenation reaction of hydrol is used as at least a part of the hydrogenated sugar.

2. The method for producing anhydrosugar alcohol according to claim 1, wherein the hydrol is the mother liquor remaining after glucose production by crystallizing crude glucose liquid to form glucose crystals and filtering the resulting product to obtain glucose crystals.

3. The method for producing anhydrosugar alcohol according to claim 1, wherein the hydrol contains 82 to 90% by weight of glucose.

4. The method for producing anhydrosugar alcohol according to claim 1, wherein the product of hydrogenation reaction of hydrol has a sorbitol content of 80% by weight or more.

5. The method for producing anhydrosugar alcohol according to claim 1, wherein 50% by weight or more of the hydrogenated sugar is derived from the product of hydrogenation reaction of hydrol.

6. The method for producing anhydrosugar alcohol according to claim 1, wherein 100% by weight of the hydrogenated sugar is derived from the product of hydrogenation reaction of hydrol.

7. The method for producing anhydrosugar alcohol according to claim 1, wherein an acid catalyst is used in the step of converting hydrogenated sugar to anhydrosugar alcohol by dehydration reaction.

8. The method for producing anhydrosugar alcohol according to claim 7, wherein the acid catalyst is sulfuric acid as a single acid catalyst.

9. The method for producing anhydrosugar alcohol according to claim 7, wherein the acid catalyst is an acid mixture of a first acid and a second acid, wherein the first acid is sulfuric acid and the second acid is one or more acids selected from the group consisting of methanesulfonic acid, p-toluenesulfonic acid, boric acid, ethanesulfonic acid, benzenesulfonic acid, naphthalenesulfonic acid and aluminum sulfate.

10. The method for producing anhydrosugar alcohol according to claim 1, wherein the dehydration reaction of hydrogenated sugar is conducted at a temperature condition of from 105 to 200° C. under a pressure condition of from 1 to 100 mmHg for 1 to 10 hours.

11. The method for producing anhydrosugar alcohol according to claim 7, wherein the resulting liquid of the dehydration reaction of hydrogenated sugar is neutralized.

12. The method for producing anhydrosugar alcohol according to claim 11, further comprising the step of distilling the neutralized resulting liquid of the dehydration reaction of hydrogenated sugar.

13. The method for producing anhydrosugar alcohol according to claim 12, further comprising the step of purifying the resulting liquid of distillation by one or more procedures selected from crystallization, decolorization and treatment with ion exchange resin.

\* \* \* \* \*